United States Patent [19]

Anthony

[11] Patent Number: 4,660,063
[45] Date of Patent: Apr. 21, 1987

[54] IMMERSION TYPE ISFET

[75] Inventor: Thomas R. Anthony, Schenectady, N.Y.

[73] Assignee: General Electric Company, Schenectady, N.Y.

[21] Appl. No.: 713,143

[22] Filed: Mar. 18, 1985

[51] Int. Cl.[4] .................. H01L 29/06; H01L 29/66; H01L 27/26
[52] U.S. Cl. .................................. 357/25; 357/55; 357/23.15; 357/29; 204/409
[58] Field of Search .................. 357/25, 55, 29, 23.15

[56] References Cited

U.S. PATENT DOCUMENTS 4,056,726 11/1977 Harchol ............................ 357/55
4,471,369 9/1984 Anthony et al. .................. 357/55
4,527,183 7/1985 Anthony et al. .................. 357/55

OTHER PUBLICATIONS

Anthony, "Forming Electrical Interconnections through Semiconductor Wafers," *J. Appl. Phys.*, 52(8), 1981, p. 5340.
Anthony, "Forming Feedthroughs in Laser-Drilled Holes . . . ", *IEEE Trans.*, CHMT-5 (1), 1982, p. 1971.
Anthony, "Diodes Formed by Laser Drilling and Diffusion," *J. Appl. Phys.*, 53(12), 1982, p. 9154.

*Primary Examiner*—Martin H. Edlow
*Assistant Examiner*—E. Fallick
*Attorney, Agent, or Firm*—Paul E. Rochford; James C. Davis, Jr.; Paul R. Webb, II

[57] ABSTRACT

Three-dimensional diode arrays have been produced in semiconductor wafers by a two-step process involving laser drilling and solid-state diffusion.

Holes are first produced in the wafer in various arrays by laser drilling. Under suitable conditions, laser drilling causes little or no damage to the wafer. Cylindrical P-N junctions are then formed around the laser-drilled holes by diffusing an impurity into the wafer from the walls of the hole. A variety of distinctly different ISFET devices is produced.

15 Claims, 19 Drawing Figures

IMMERSION TYPE ISFET

BACKGROUND OF THE INVENTION

The present invention relates generally to semiconductor devices for sensing chemical concentration or activity, and more particularly to a method for fabricating ion-sensitive field-effect transistor devices having a nonplanar structure and the devices produced thereby.

In recent years there has been a growing need for compact sensors of chemical concentration and activity, particularly for use in aqueous solutions. As a result of such need there has been considerable research and development effort in the area of chemically sensitive semiconductor devices. Much of this effort has centered around a device called the ion-sensitive field-effect transistor (herein ISFET). The operation of the ISFET will now be briefly explained with the aid of FIG. 1, which shows a known ISFET structure fabricated with a conventional planar silicon technology similar to that used for producing metal-oxide-semiconductor field-effect transistors (MOSFET).

Referring now to FIG. 1, the ISFET device 10 produced by the conventional technology includes a relatively lightly doped P-type (P−) monocrystalline silicon body region 11 into which are diffused two relatively heavily doped N-type (N+) regions 12 and 13. The body region 11 may be a portion of a substrate wafer or an epitaxially grown layer. The regions 12 and 13, which respectively serve as the source and drain regions of the device, are diffused into the body 11 from its top surface 14. A portion of that surface 15 between the source and drain regions 12 and 13 is covered with a relatively thin, thermally grown silicon dioxide layer 16. The remainder of the top surface of the device 10 is covered with a relatively thick silicon dioxide layer 17, through which contact apertures 8 and 9 are opened to expose the surfaces of the source and drain regions 12 and 13, respectively. Strip-like metal layers 6 and 7 are then deposited over the source and drain regions 12 and 13, respectively, making ohmic contact to those regions through the contact apertures 8 and 9. The metal layers 6 and 7 serve as the source and drain contacts, respectively, while the silicon dioxide layer 16 serves as the ion-sensitive insulating layer of the ISFET device 10.

In the absence of an electric field at the silicon surface 15 beneath the oxide layer 16, the ISFET device 10 exhibits an extremely high electrical resistance between its source and drain contacts 6 and 7. If the device 10 is immersed in an aqueous solution, the silicon dioxide layer manifests hydrating properties similar to that of the glass membrane of the well known glass electrode PH measuring device. If the solution contains cation activity, a double charge layer forms at the interface of the solution and the oxide layer 16, establishing an electric field at the silicon surface 15. In the event that the electric field at the silicon surface 15 becomes sufficiently large, an inversion layer or channel is induced in the silicon body 11 adjacent to the surface 15 causing the resistance between the source and drain contacts 6 and 7 of the device 10 to decrease. The threshold electric field at which the channel is induced depends on the surface doping concentration of the silicon body 11, which may be adjusted during fabrication of the device 10. Since the conductance of the channel depends on the electric field at the silicon surface 15, which in turn depends on the ion activity in the solution, the resistance between the source and drain contacts 6 and 7 provides a measure of the ion activity in the solution.

The ISFET provides two major advantages over other known ion activity sensors, such as ion selective electrodes. Firstly, a reference electrode is not required when measurements are made with the ISFET. Secondly, the responsive variable of an ISFET device is a relatively low, ohmic resistance, which can be easily measured with precision.

However, the ISFET device fabricated by conventional methods, such as that illustrated in FIG. 1, has a serious shortcoming in that its planar structure presents formidable packaging problems. Owing to the source and drain contacts 6 and 7 of the device being on the same side of the substrate chip as the ion-sensitive insulating layer 16, it is very difficult to reliably isolate the contacts 6 and 7 from the solution into which the layer 16 is immersed. Isolation of the source and drain contacts 6 and 7 from the chemically active solution is of critical importance not only for avoiding an undesirable parasitic conducting path through the solution, but also for preventing corrosion of the contacts by the solution, which can lead to failure of the device. Accordingly, a need clearly exists for a method of fabricating ISFET devices which provides device structures amenable to effective and reliable isolation of the source and drain contacts of the device from the solution into which the ion sensitive portion of the device is immersed.

Holes have been drilled in semiconductor wafers heretofore.

Three articles of the present inventor deal with the subject of wafers and laser drilled holes in such wafers. They are as follows:

(1) "Forming electrical interconnections through semiconductor wafers" by T. R. Anthony, J. Appl. Physics, 52 (8), 5340 (1981).

(2) "Forming Feedthroughs in Laser-Drilled Holes in Semiconductor Wafers by Double-Sided Spattering" by T. R. Anthony, IEEE Trans. CHMT-5 (1), 1971 (1982).

(3) "Diodes formed by Laser Drilling and Diffusion" by T. R. Anthony, J. Appl. Phys. 53 (12), 9154 (1982).

SUMMARY OF THE INVENTION

The foregoing and other shortcomings of the prior art have been overcome by the present invention which in one aspect is a method for fabricating ISFET devices in which one or more bores are formed in a semiconductor substrate body to effect nonplanar device structures having source and drain contacts that are amenable to effective and reliable isolation from a chemically active solution into which an ion-sensitive insulating layer of the device is immersed. The bores are used for diffusing relatively heavily doped impurity zones, each of which concentrically surround a bore and extend through the entire thickness of the substrate body between opposing major surfaces thereof. The impurity zones, either singly or overlapped with one or more other zones, serve as the source and drain regions of an ISFET device in which the ion-sensitive insulating layer is formed on one side of the substrate body and the source and drain contacts are formed on the opposite side of the substrate body. The bores used to effect the diffusion of the impurity zones are preferably formed by laser drilling to have a high aspect ratio and to extend either completely through the thickness of the substrate body or to within an impurity diffusion distance of the thickness of the body.

In other embodiments, one or more bores of relatively large cross-sectional area are formed to extend through the entire thickness of the substrate body between opposing major surfaces thereof and to transversely or longitudinally intersect spaced-apart source and drain regions therein. The inner surfaces of such bores support ion-sensitive insulating layers to provide device structures that are adapted for making measurements on solutions flowing through such bores. The cross-sectional area of each such bore is determined by the desired flow rate through the bore. Large cross-sectional area bores are preferably formed by laser drilling. Such bores may be dormed by drilling with a high laser power or by drilling multiple overlapping bores along a circular path.

Another aspect of the present invention is the unique and advantageous ISFET device structure produced by the foregoing method. In an exemplary embodiment such structure comprises spaced-apart source and drain regions of generally uniform cross-section extending through the entire thickness of a semiconductor substrate body, spaced-apart contacts to the source and drain regions located on one major surface of the substrate body and an ion-sensitive insulating layer on an opposing major surface of the substrate body. In another exemplary embodiment the ISFET structure of the present invention comprises spaced-apart source and drain surface regions oppositely disposed adjacent respective ones of opposing major surfaces of a semiconductor substrate body, a relatively large cross-sectional area bore extending through the substrate body between the major surfaces and transversely intersecting the source and drain regions, contacts to the source and drain regions located on respective ones of the major surfaces and an ion-sensitive insulating layer covering the inner surface of the bore. In yet another exemplary embodiment, the ISFET structure of the present invention comprises spaced-apart source and drain regions each having a generally uniform cross-section and extending through the entire thickness of a semiconductor substrate body between opposing major surfaces thereof, a relatively large cross-sectional area bore extending through the entire thickness of the substrate body between the major surfaces and longitudinally intersecting the source and drain regions, spaced-apart contacts to the source and drain regions adjacent one of the major surfaces, and an ion-sensitive insulating layer covering the inner surface of the bore.

DETAILED DESCRIPTION OF THE PREFERRED EMBODIMENTS

Figure 1:
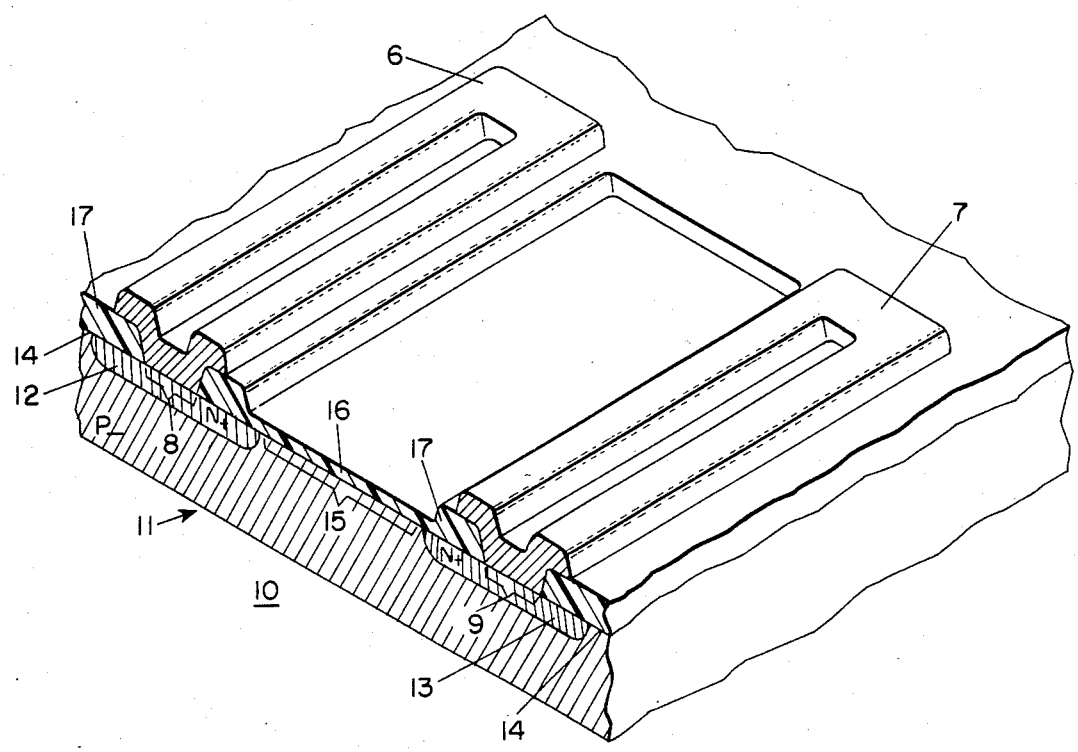
FIG. 1 is a partially sectional, isometric view of an ISFET device fabricated with a conventional planar silicon technology.

Exemplary embodiments of the present invention will now be explained with reference to the appended figures of the drawing in which the same reference numerals and characters are used to denote like regions, zones, dimensions and features of the illustrated device.

Figure 2:
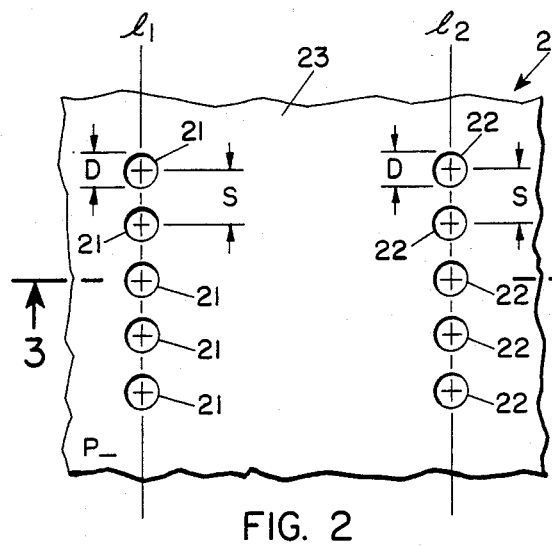
FIG. 2 is a top view of a portion of a $P_-$-type silicon substrate body in which there have been formed two rows of high-aspect-ratio bores.
Figure 3:
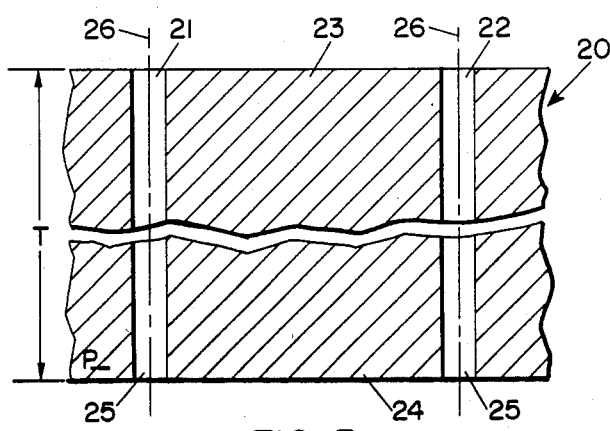
FIG. 3 is a cross-sectional view of the substrate body of FIG. 2 taken along plane 3—3 of FIG. 2 illustrating the bores extending through the entire thickness of the body between major surfaces thereof.

Referring now to FIGS. 2 and 3, two spaced-apart opposing rows of bores 21 and 22 are formed in a semiconductor body 20. Each row comprises five bores generally disposed along a respective one of two mutually parallel straight lines $l_1$ and $l_2$. The bores 21 and 22 are formed to have high aspect ratios (i.e., a length to diameter ratio of greater than 6) and to extend through the entire thickness T of the body 20 between two opposing major surfaces 23 and 24 thereof. The semiconductor body 20 comprises a portion of a substrate wafer of single-crystalline silicon having a thickness T in the range of 12 to 20 mils (1 mil=0.001 inches) and a substantially uniform boron impurity concentration in the range of $1 \times 10^{13}$ to $4 \times 10^{14}$ atoms/cm$^3$. The major surfaces 23 and 24 of the body 20 are substantially parallel to one another and are advantageously oriented in either the $<111>$ or $<100>$ crystallographic directions.

The bores 21 and 22, which are interior lengthwise cylindrical cavities of generally circular cross-section, are formed by a technique called "laser drilling" where a high intensity, forcussed laser beam is used to excavate cavities in the substrate body 20 through melting and removal of the material of the body on the vicinity of the beam. The laser used may be an ESI, Inc. Model 25 Laser Scribing System modified with a 10 watt (maximum) optoacoustic Q-switched Nd:YAG head manufactured by U.S. Laser Corp. The laser is advantageously operated in a repetitively Q-switched mode with a focussed beam diameter of about 20 μm, a depth of focus of about 250 μm, a pulse duration of about 200 nanoseconds, and a repetition rate of about 3 KHz. With the average power of the laser set at about 2 watts and the laser pulse-width and delay between successive pulses set at about 5 msec and 10 msec, respectively, the bores 21 and 22 can be "drilled" at a rate of approximately five per second.

During the laser drilling process, the semiconductor substrate body 20 is advantagesouly held in a vacuum chuck which does not have any reflective metallic supporting surfaces adjacent the body to cause unwanted reflections of the laser beam, particularly as the beam closely approaches the bottom surface of the body. Such reflections can produce irregularly sized bores. A novel chuck having such a feature is disclosed in our patent application Ser. No. 245,776 filed Mar. 20, 1981 and now abandoned. Another feature of the inventive chuck is that it permits debris from the laser drilling to be ejected downwardly away from the bottom surface 24 of the substrate body 20, thus facilitating the formation of a clean, well-defined aperture on the bottom surface 24 when the bores are drilled completely through the body 20.

When the laser is operated in the above-described manner, the bores 21 formed by laser drilling have substantially circular cross-sections of uniform diameter, and the inner surfaces 25 of the bores 21 and 22 are substantially circular cylindrical surfaces. However, the present invention is not limited to bores which are circular cylindrical cavities, as cavities of other cross-sectional shapes formed by, for example, changing the operating parameters of the laser may be used. It is also advantageous to form the bores such that their axes 26 are mutually parallel and perpendicular to the major surfaces 23 and 24 of the body 20.

Some surface blemishes, caused by the fallout of debris from the bores during drilling, may be observed when laser drilling is performed on uncoated silicon wafers. These blemishes can be eliminated by precoating both sides of the wafer with black acrylic spray paint prior to drilling and removing the coating with toluene after drilling. In this manner the debris from drilling the bores are stripped away with the paint coating. Other coatings such as photoresist, parafin, or silicon grease should be equally suitable for removing the debris, but are less easily stripped than acrylic spray paint.

Each of the bores 21 and 22 has a diameter D of approximately 1 mil, and the center-to-center spacing s between adjacent bores in each row is approximately 2 mils.

After the drilling operations, the body should be checked to determine the extent to which any stress or strains were introduced into the regions adjacent to the bores by the laser drilling operation. Polarized infrared light may be used to check for the presence of stress, since if stress is present, the silicon becomes birefringent and patterns indicative of stress are observed.

Two methods may be advantageously used to check for the presence of dislocations which are indicative of residual strains in the silicon body caused by the laser drilling. In the first method dislocations are decorated by copper precipitates. A saturated solution of Cu(NO$_3$)$_2$ is applied to the top surface through which the laser beam entered the body. The body and solution are then heated to 900° in dry hydrogen for one hour and quenched in air. Thereafter, inspection with infrared light reveals the presence or absence of copper-decorated dislocations, which indicate whether or not the regions adjacent to the holes are strain-free. In the second method, Dash's etch (1 part HF, 3 parts HNO$_3$ and 10 parts acetic acid) is applied to the top surface at room temperature. The presence or absence of any aggressive localized pitting of the silicon body adjacent to the bore caused by the etch indicates whether or not there are any dislocations.

In general, strains and stresses in the regions adjacent to the bore may be avoided by proper selection of laser-drilling parameters and fixturing of the wafer. The use of short laser pulses minimizes diffusion of heat into the silicon surrounding the bore and, therefore, also minimizes any thermal stress and the resulting damage to the silicon lattice.

Figure 4:
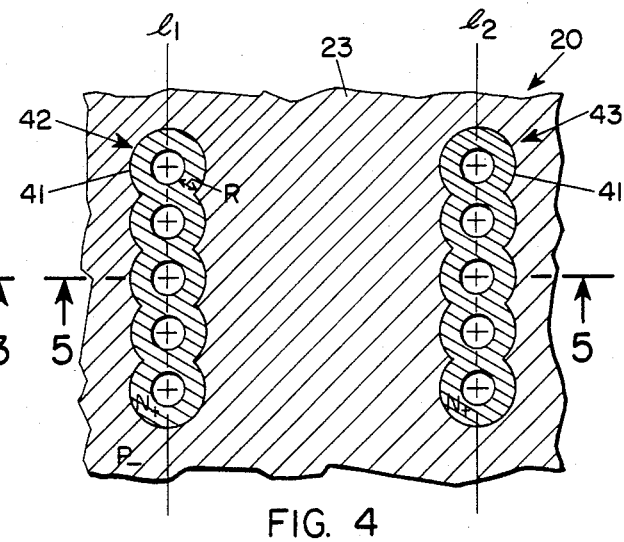
FIG. 4 is a top view of the substrate body of FIG. 2 after the formation of $N_+$-type impurity zones concentrically surrounding each bore, each zone overlapping with one or more adjacent zones in its respective row to form two continuous $N_+$-type impurity regions.
Figure 5:
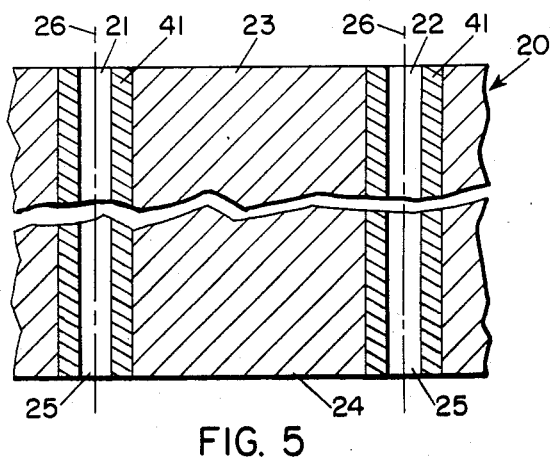
FIG. 5 is a cross-sectional view of the silicon body of FIG. 4 taken along plane 5—5 of FIG. 4.

Turning now to FIGS. 4 and 5, following the formation of the bores 21 and 22, the semiconductor body 20 undergoes processing to form relatively high impurity concentration N-type zones 41 of generally uniform cross-section and substantially concentric with respective ones of the bores 21 and 22. An appropriate N-type impurity is diffused into the substrate body 20 through the inner surface 25 of each bore. As used hereinafter, the term "concentric" refers to two or more cylindrical figures having a common axis of symmetry.

There are several diffusion techniques which may be used to form the impurity zones 41. One technique is to use a liquid "spin-on" solid state source of diffusible N-type impurity such as phosphorus or arsenic. Using this technique, the semiconductor body 20 is held in a vacuum chuck following the formation of the bores 21 and 22, and several drops of the spin-on liquid source are applied to the top surface 23 of the body 20. It is generally not necessary to spin the substrate body 20 during such application, in as much as the spin-on liquid spread uniformly over the top surface 23, the inner surfaces 25 of the bores and bottom surface 24 under the combined actions of surface tension, capillary force and the vacuum.

Following the application of the spin-on source, it is generally desirable to bake the coated body 20 at a relatively low temperature and short duration (e.g., 150° C. for 1 hour) in a nitrogen atmosphere to drive off any residual solvent in the coating. Thereafter the coated body 20 is subjected to pre-deposit and drive-in bake cycles in an oxidizing ambient (e.g., a flowing mixture of $O_2$ and $N_2$) so as to diffuse the N-type impurities into the body 20 through the inner surface 25 of each of the bores 21 and 22 and form a PN junction in the body at a radial distance R in the range of 1 to 10 mils beyond the inner surface 25, as shown in FIG. 4. The surface impurity concentration of the N-type zones 41 is advantageously greater than $10^{18}$ atoms/cm$^3$. The temperatures and durations of the bake cycles as well as the composition and flow rate of the gaseous ambient used for achieving the desired junction depth and surface impurity concentration may be readily determined by those skilled in the art of semiconductor devices from known diffusion data. Therefore, the details of such determination are omitted. However, it is noted that by diffusing the impurities into the body 20 through the inner surfaces 25 of the bores 21 and 22, the impurities have simultaneous access to the entire thickness of the body 20 and the diffusion times required to form deep impurity zones are considerably less than that required by conventional techniques.

Each of the $N_+$-type impurity zones 41 concentrically surround a respective one of the bores 21 and 22 and extend through the entire thickness of the substrated body between the major surfaces 23 and 24. Owing to the close spacing of the bores 21 and 22 in each row, the neighboring impurity zones 41 in each row overlap to form continuous $N_+$-type source and drain regions 42 and 43, respectively. In general, the ISFET device is bilateral in that the source and drain contacts of the device are interchangeable. Therefore, whether a device region connected to such a contact is denominated a source or a drain region depends on how that region is biased with respect to the other regions of the device during operation. However, for purposes of explanation, it is assumed that the ISFET device whose fabrication is being illustrated will be operated in such a manner that region 42 is the source region and region 43 is the drain region.

Those skilled in the art of semiconductor devices will recognize that unless special measures are taken, the impurity will also diffuse into the body from the other exposed surfaces thereof, e.g., the top and bottom surfaces 23 and 24. Therefore, after the diffusion operation, the layer-like impurity zones that are formed adjacent those surfaces may be removed by conventional mechanical polishing techniques. Alternatively, the formation of the layer-like zones may be prevented by masking those regions of the top and bottom surfaces 23 and 24 where impurity diffusion is not desired by means of conventional diffusion masking techniques, such as the formation of appropriately patterned silicon dioxide layers on those surfaces prior to diffusing the impurities.

Another technique for forming substantially equivalent $N_+$-type impurity zones 41 is to use a gaseous diffusion source of N-type impurities. For example, the substrate body 20 may be heated at an appropriate temperature and for an appropriate time in the presence of a carrier gas containing phosphorous oxychloride ($POCl_3$). The carrier gas is advantageously a flowing mixture of nitrogen and oxygen. The temperature and duration as well as the composition and flow rate of the carrier gas used for such diffusion to achieve the desired junction depth and surface impurity concentration may be readily determined by those skilled in the art of semiconductor devices. Therefore, the details of such determination are omitted.

Alternatively, the above-described carrier gas may contain a different N-type impurity, such as an arsenic or antimony compound.

After the diffusion operation, the top and bottom surfaces 23 and 24 of the substrate body 20 may be mechanically polished to a depth of about 60 μm to remove any layer-like zones formed adjacent to those surfaces. The above-described method for forming high-aspect-ratio diffused zones in a semiconductor body by means of drilling bores in the body and diffusing impurities into the body through the inner walls of the bores is disclosed and claimed in the above-referenced application Ser. No. 267,235 filed May 26, 1981 and abandoned in favor of a continuation-in-part application Ser. No. 544,935 filed Oct. 24, 1983 now issued U.S. Pat. No. 4,570,173 issued Feb. 11, 1986 which is incorporated herein by reference.

Figure 6:
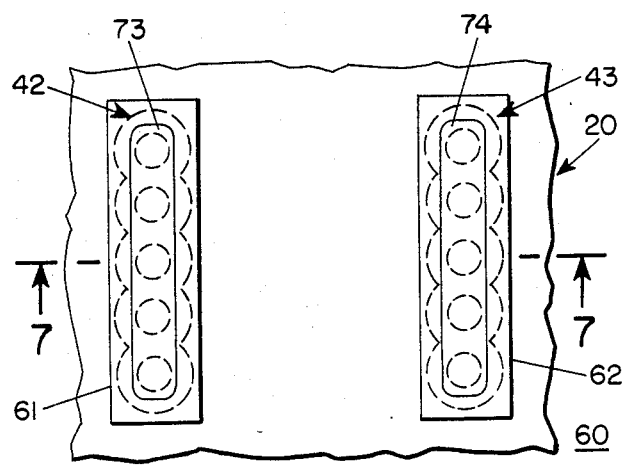
FIG. 6 is a top view of an ISFET device fabricated according to one embodiment of the present invention.
Figure 7:
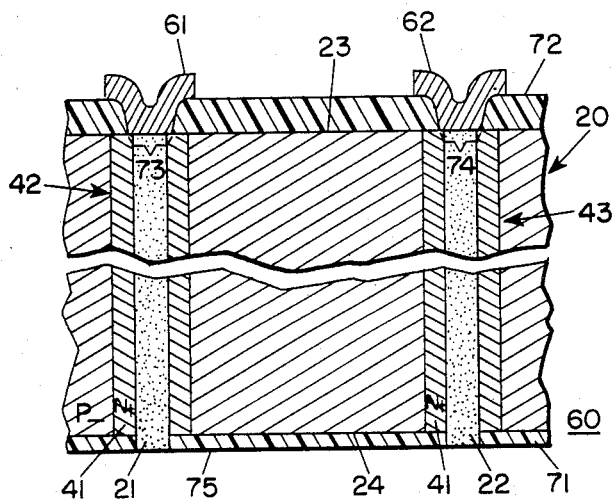
FIG. 7 is a cross-sectional view of the ISFET device of FIG. 6 taken along plane 7—7 of FIG. 6 illustrating a relatively thin silicon dioxide layer on the bottom surface of the device, a relatively thick silicon dioxide layer on the top surface of the device, source and drain regions extending between the top and bottom surfaces, contact apertures in the relatively thick silicon dioxide layer, and source and drain contacts adjacent the top surface of the device.

Referring now to FIGS. 6 and 7, following the formation of the N-type zones 41, the substrate body 20 undergoes further processing to form a relatively thin silicon dioxide layer on its bottom surface 24 and electrical contacts 61 and 62 to the source region 42 and the drain region 43, respectively, at its top surface 23. The thickness of the oxide layer 71 is advantageously in the range of 1000 Angstroms to 7000 Angstroms and formed by thermal oxidation at 1000° C. in the presence of steam at a pressure of 1 atm. Under such conditions, the approximate times required for growing oxide layers of various thicknesses are as follows: (1) 6 min. for 1000 Angstroms; (2) 15 min. for 2000 Angstroms; (3) 30 min. for 3000 Angstroms; (4) 50 min. for 4000 Angstroms; (5) 70 minutes for 5000 Angstroms; (6) 100 min. for 6000 Angstroms; and (7) 120 min. for 7000 Angstroms.

The contacts 61 and 62 are advantageously formed by first growing a relatively thick (e.g., 10,000 Angstroms or greater) silicon dioxide layer 72 over the top surface 23 of the substrate body 20. It is desirable to partially grow the thick oxide layer 72 in the same oxidation step used to grow the thin oxide layer 71. Following its formation, the thin oxide layer 71 is masked with a layer of photoresist to prevent further oxidation and the substrate body 20 is subjected to further steam oxidation under the same conditions until the thick oxide layer 72 reaches the desired thickness. Thereafter, the thick oxide layer 72 is patterned by known photolithographic and etching techniques to open contact windows 73 and 74 exposing portions of the top surface 23 over the source region 42 and the drain region 43, respectively. It is noted that the contact windows 73 and 74 do not overlap the P-type regions of the substrate body 20.

The contacts 61 and 62 may be formed by melting gold-(2 wt %-antimony) alloy into the silicon surface in a hydrogen atmosphere at a temperature between 400° and 500° C. Wires made of that alloy can serve as the contact material as well as the signal leads of the device.

Alternatively, a layer of an appropriate metal, such as aluminum, is vacuum deposited over the top surface 23 of the body and patterned by conventional photolithographic etching techniques to form strip-like contacts 61 and 62. Where aluminum is used as the contact metal, the impurity concentration at the surfaces of the source and drain regions 42 and 43 should be on the order to $10^{20}$ atoms/cm$^3$ or greater to assure good ohmic contacts. If necessary, the surface impurity concentration of the source and drain regions 42 and 43 in the areas exposed by the contact apertures 73 and 74 may be increased, for example, by an additional masked diffusion step prior to the deposition of the aluminum layer.

The ISFET device 60 fabricated by the foregoing process has its source and drain contacts 61 and 62 situated adjacent the top surface 23 of the substrate body 20 and its ion-sensitive oxide layer 71 situated adjacent the bottom surface 24 of the body. Such a nonplanar device structure can be easily packaged to effectively and reliably isolate the contacts 61 and 62 from a solution being measured while leaving the oxide layer 71 exposed to the solution. For example, the entire top surface of the device can be encapsulated with appropriate provisions for running lead wires to the source and drain contacts 61 and 62.

The bores 21 and 22 are advantageously sealed to prevent the solution being measured from reaching the contacts 61 and 62 through the bores. The filling and sealing of the bores 21 and 22 is easily accomplished by applying an appropriate liquid sealing substance, e.g., silicon-polyimide liquid or an epoxy liquid, to the openings of the bores 21 and 22. The liquid sealing substance is drawn by capillary force into the bores 21 and 22 where it is then cured in place. It is noted that the sealing substance used must be resistant to attack by the chemicals in the solution to be measured by the device.

Figure 8:
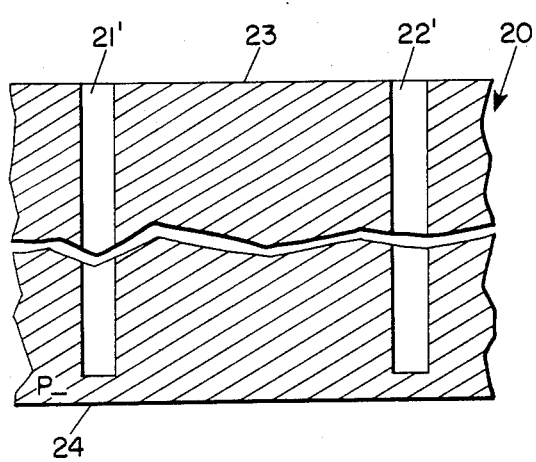
FIG. 8 is a cross-sectional view of a portion of a P-type silicon substrate body in which there have been formed high-aspect-ratio blind bores.

According to the present invention, the bores 21 and 22 around which the N-type impurity zones 41 are formed need not extend completely through the thickness of the substrate body 20. In some instances, it may be desirable to use blind bores 21' and 22' drilled from the top surface 23 of the body 20 to a uniform predetermined depth as shown in FIG. 8. For example, the substitution of blind bores in the foregoing process makes sealing of the bores unnecessary and facilitates the use of a vacuum chuck to hold the substrate body 20 during processing. Blind bores of a desired depth may be reproduceably formed by the above-described pulsed laser drilling technique by carefully controlling the number of laser pulses used to drill each bore. A calibration curve of depth-of-bore versus number of laser pulses may be empirically derived to aid the practitioner in accurately drilling blind bores of desired depths.

Figure 9:
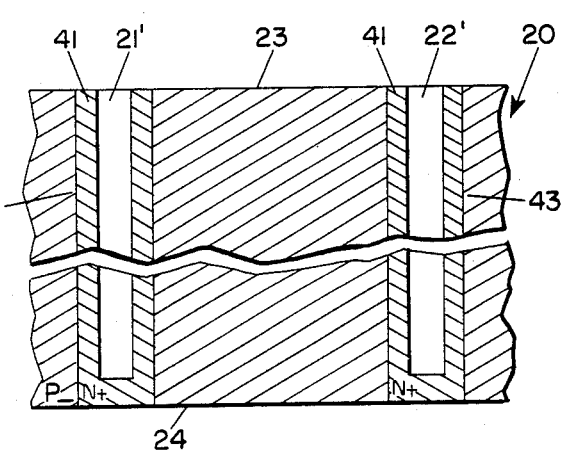
FIG. 9 is a cross-sectional view of the silicon body of FIG. 8 following the formation of $N_+$-type impurity zones which extend through the entire thickness of the body.

Turning now to FIG. 9, N-type impurity zones 41 which extend through the entire thickness of the substrate body 20 may be formed around blind bores 21' and 22' by drilling each bore to within an impurity diffusion distance from the bottom surface 24 of the body 20. The impurity diffusion distance is the distance that a particular impurity diffuses beyond the bottom of the blind bores 21' and 22' during the formation of the $N_+$-type impurity zones 41. FIG. 9 depicts the body 20 following the formation of the impurity zones 41 after the removal of the impurity layers which are formed adjacent the top and bottom surfaces of the body during the diffusion step.

Figure 10:
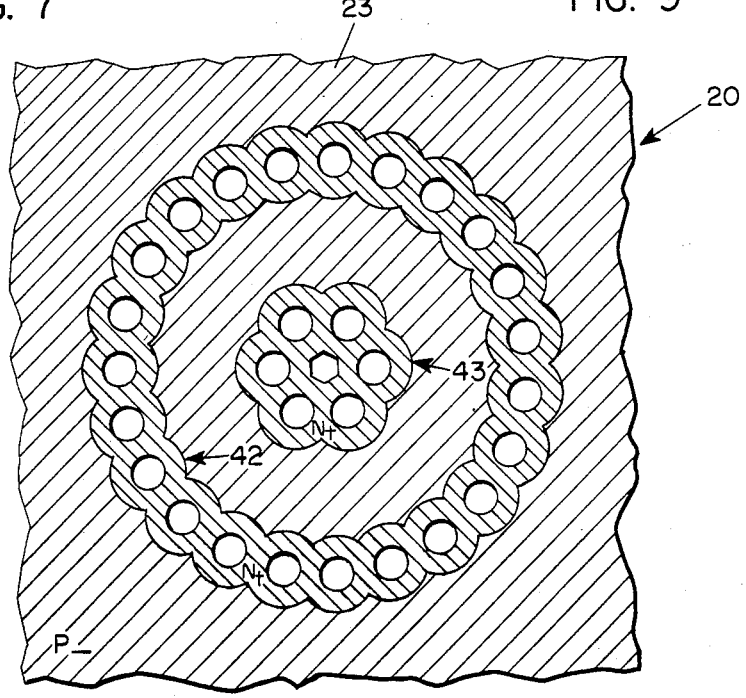
FIG. 10 is a top view of a portion of a $P_-$-type silicon body in which there have been formed two groups of high-aspect-ratio bores and corresponding $N_+$-type impurity zones, the bore in each group being disposed along a respective one of two concentric circular paths, each impurity zone overlapping with adjacent zones in its respective group to form continuous, concentric circular impurity regions.

Referring again to FIG. 4, the bores 21 and 22 and their corresponding impurity zones 41 that comprise the source and drain regions 42 and 43 of the device need not be disposed along straight lines as shown, but may instead be arranged in other configurations in which spaced-apart, continuous source and drain regions are each formed by one or more impurity zones. For example, the bores and their corresponding zones may be disposed along respective concentric circular paths as shown in FIG. 10.

The separation between the source and drain regions is selected to provide a desired channel resistance range for the device. In general the channel resistance for a given electric field strength at the semiconductor surface beneath the ion-sensitive insulating layer is proportional to the separation between the source and drain regions and inversely proportional to the dimensions of the opposing sides of those regions. The calculation of the channel resistance for a given source and drain configuration will be known to those skilled in the art of semiconductor devices.

Referring again to FIG. 7, as already mentioned the silicon dioxide layer 71 of the ISFET device 60 fabricated in accordance with the present invention by the foregoing process serves as an ion-sensitive insulating layer of the device in that when the exposed surface 75 of the oxide layer 71 is immersed into a solution, an electric potential difference develops across the layer 71 which depends on the ions present in the solution. In general, the use of the silicon-dioxide layer 71 as the ion-sensitive insulating layer provides a device that responds to a broad range of cations. However, by using appropriately selected other materials for the ion-sensitive insulating layer of the ISFET 60, a device sensitive to a particular ion or a particular class of ions may be achieved. For example, various glass compositions, crystalline materials and composite materials are known to be useful as membranes in ion-selective electrodes. Some of those materials may be suitable for substitution as the ion-sensitive insulating layer in the ISFET 60.

Figure 11:
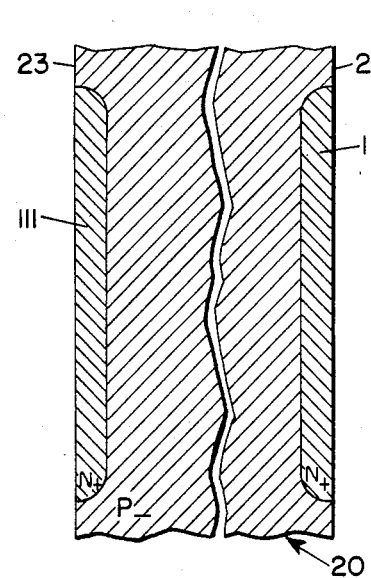
FIG. 11 is a cross-sectional view of a portion of a $P_-$-type silicon body in which there have been formed two $N_+$-type surface impurity regions adjacent respective ones of two opposing major surfaces of the body, the impurity regions being spaced apart and disposed opposite one another.
Figure 12:
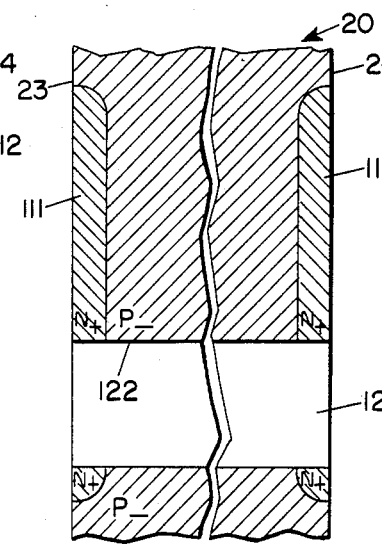
FIG. 12 is a cross-sectional view of the silicon body of FIG. 11 following the formation of a bore which extends entirely through the thickness of the body and transversely intersects the two surface impurity regions.
Figure 13:
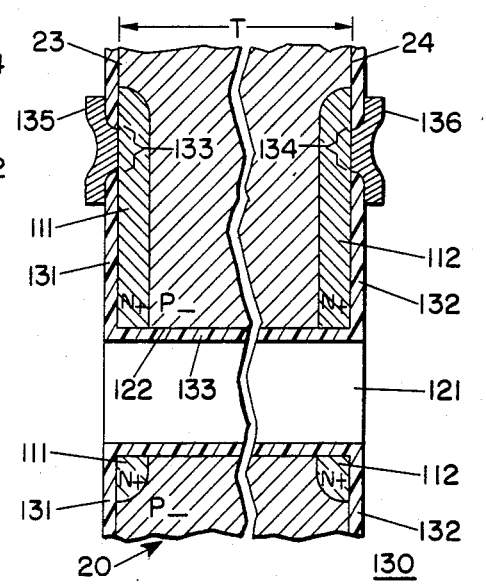
FIG. 13 is a cross-sectional view of an ISFET device fabricated according to another embodiment of the present invention illustrating silicon dioxide layers on the two major surfaces of the body and on the inner surface of the bore, contact apertures in respective ones of the silicon dioxide layers on the two major surfaces, and source and drain contacts adjacent respective ones of the two major surfaces.

FIGS. 11 through 13 illustrate a method for fabricating an ISFET device according to another exemplary embodiment of the invention. This method provides an ISFET structure which is adapted for measuring ion concentration or activity in flowing solutions. Referring now to FIG. 11, two relatively shallow, $N_+$-type regions 111 and 112 are formed adjacent the major surfaces 23 and 24, respectively, of a P-type silicon substrate body 20 having the same characteristics as described above in connection with the preceding embodiment of the invention. The impurity regions 111 and 112, which are disposed opposite one another, are formed by conventional diffusion or ion implantation of an appropriate N-type impurity, such as phosphorous, arsenic or antimony, to depths in the range of 1 to 4 mils and to surface impurity concentrations of at least $1 \times 10^{18}$ atoms/cm. These regions may extend over the entire major surfaces 23 and 24 of the body 20 or over only a portion thereof.

With reference now to FIG. 12, following the formation of the impurity regions 111 and 112, a bore 121 is formed extending through the entire thickness of the substrate body 20 between the surfaces 23 and 24. The bore 121 transversely intersects and penetrates both impurity regions 111 and 112. The cross-sectional area of the bore 121 is determined by the desired flow rate of solution through the bore, as well as other considerations such as the possible presence of solid particles in the solution which may clog or block the bore unless its cross-sectional area is large enough to pass such particles. For a bore having a circular cross-section, the flow rate Q through the bore is approximately given by $$Q = \Delta p D^4 / (128 \mu L), \quad (1)$$

where D is the diameter of the bore, L is the length of the bore, $\Delta p$ is the pressure difference between two ends of the bore, and $\mu$ is the viscosity of the solution. It should be noted that in some instances it may be desirable to form more than one bore to achieve a desired flow rate. Where multiple bores are used, each bore must transversely intersect and penetrate both impurity layers 111 and 112.

The bore 121 is advantageously formed using the laser drilling technique described above. A bore with a large cross-section area may be formed by drilling with a relatively high laser power or by drilling a series of small, overlapping bores along a circular path. Alternatively, a large cross-sectional area bore may be formed by first drilling a small bore and then enlarging that bore using known selective etching techniques. The bore 121 may also be formed by known ultrasonic drilling techniques.

Turning now to FIG. 13, after forming the bore 121 silicon dioxide layers 131, 132 and 133 are grown on the two surfaces 23 and 24 of the substrate body 20 and on the inner surface 122 of the bore 121, respectively, using the steam oxidation techniques described above. Following the oxidation step, contact apertures 133 and 134 are opened in the oxide layers 131 and 132, respectively, using conventional photolithographic and etching techniques. The contact apertures 133 and 134 expose portions of the surfaces of the $N_+$-type impurity regions 111 and 112, respectively, where electrical contacts are to be made. Thereafter, contacts 135 and 136 are formed using the metallization techniques described above. Assuming that region 111 is the source region and region 112 is the drain region, the contacts 135 and 136 respectively serve as the connection means for the source and drain of the ISFET device 130 fabricated by the foregoing process.

The silicon dioxide layer 133 on the inner surface 122 of the bore 121 serves as the ion-sensitive insulating layer which contacts the flowing solution being measured. As explained above in connection with the previous embodiment, the oxide layer 133 may be substituted with a layer of appropriate insulating material having ion selective membrane properties.

It is desirable to space the contacts 135 and 136 sufficiently far from the bore 121 to permit effective packaging of the device 130. It is noted that the nonplanar ISFET structure produced by the foregoing process permits packaging of the device for effective and reliable isolation of the source and drain contacts 135 and 136 from the solution being measured.

The channel resistance of the ISFET 130 for a given electric field strength at the inner surface 122 of the bore 121 is generally proportional to the spacing between the source and drain regions 111 and 112 and inversely proportional to the perimeter of the bore 121. The calculation of such channel resistance will be known to those skilled in the art of semiconductor devices. The channel resistance maybe adjusted by varying the thickness T of the substrate body 20 or the depths of the source and drain regions.

Figure 14:
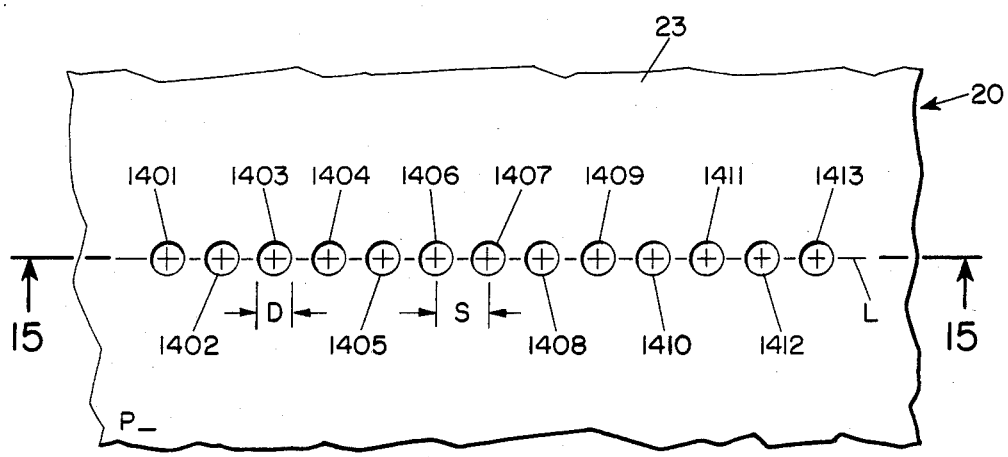
FIG. 14 is a top view of a portion of a $P_-$-type silicon body in which there have been formed a multiplicity of closely spaced, high-aspect-ratio bores disposed along a straight line.
Figure 15:
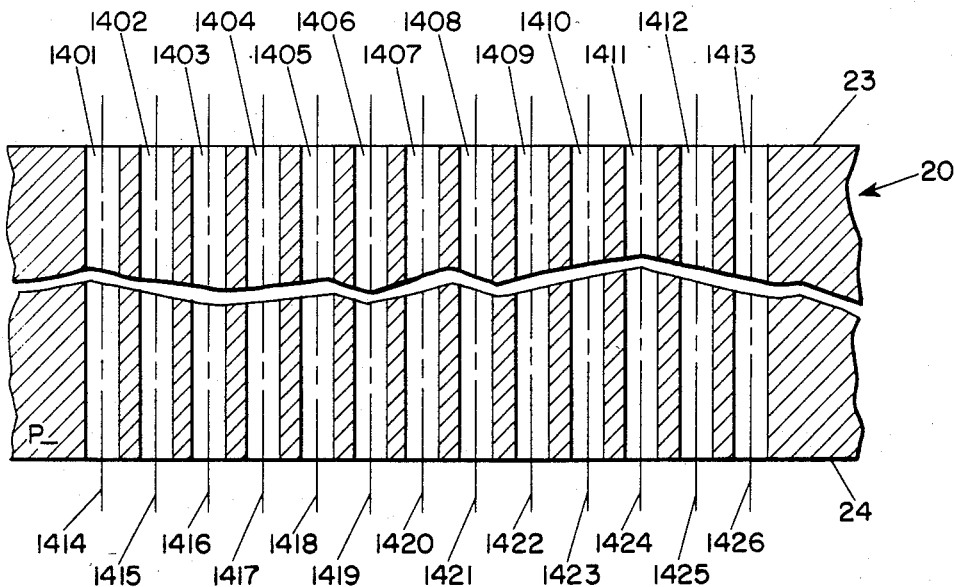
FIG. 15 is a cross-sectional view of the silicon body of FIG. 14 taken along plane 15—15 of FIG. 14 illustrating the bores extending through the entire thickness of the body between two major surfaces thereof.

FIGS. 14 through 18 illustrate a method for fabricating an ISFET device according to still another exemplary embodiment of the present invention. This method yields another ISFET structure which is adapted for measuring ion concentration or activity in flowing solutions. Referring now to FIGS. 14 and 15 thirteen high-aspect-ratio bores 1401 to 1413 are formed in a silicon substrate body having the same characteristics as described above in connection with the embodiment illustrated by FIGS. 2 through 7. The bores 1401 to 1413, which are generally disposed along a straight line L, are advantageously formed by the above-described laser drilling technique to extend through the entire thickness of the body 20 between the major surfaces 23 and 24. Each of the bores 1401 to 1413 has a diameter D of approximately 1 mil, and the center-to-center spacing S between adjacent bores is approximately 2 mils. It is advantageous to form the bores such that their axes 1414 to 1426 are mutually parallel and perpendicular to the major surfaces 23 and 24 of the substrate body 20.

Figure 16:
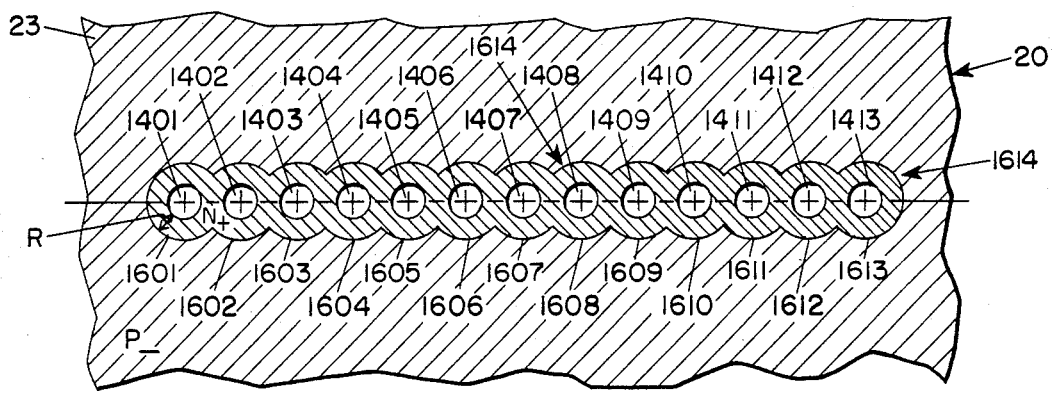
FIG. 16 is a top view of the silicon body of FIG. 14 following the formation of $N_+$-type impurity zones concentrically surrounding each bore, each zone overlapping with one or more adjacent zones to form a continuous $N_+$-type impurity region.

Turning now to FIG. 16, after the bores 1401 to 1413 are drilled, the substrate body 20 undergoes processing to form relatively high impurity concentration N-type zones 1601 to 1613 of generally uniform cross-section extending through the entire thickness of the body 20 between the surfaces 23 and 24. The impurity zones 1601 to 1613, each of which concentrically surrounds a respective one of the bores 1401 to 1413, are formed by the diffusion techniques described above in connection with the embodiment illustrated in FIGS. 2 through 7. It is advantageous to form the impurity zones to extend radially into the body 20 to a distance R in the range of 1 to 10 mils.

Owing to the close spacing of the bores 1401 to 1413, neighboring ones of the impurity zones 1601 to 1613 overlap to form a continuous $N_+$-type impurity region 1614.

Figure 17:
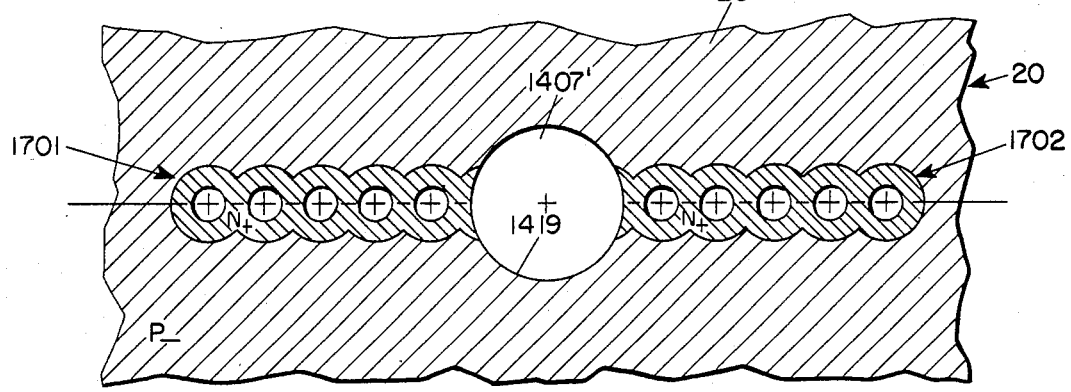
FIG. 17 is a top view of the silicon body of FIG. 16 after the enlargement of one of the bores illustrating the enlarged bore separating and longitudinally intersecting two continuous $N_+$-type impurity regions.

Referring now to FIG. 17, subsequent to the diffusion of the impurity zones 1601 to 1613, one of the bores 1407 is enlarged such that it separates the impurity region 1614 into two regions 1701 and 1702. The enlarged bore 1407' longitudinally intersects the $N_+$-type impurity regions 1701 and 1702 in that the bore is contiguous with both regions along its entire length.

The enlargement of the bore 1407 is accomplished by selective etching of the bore using known techniques. Alternatively, the bore 1407 may also be enlarged by redrilling with the laser at higher powers or by drilling a series of overlapping, high-aspect-ratio bores along a concentric circular path as mentioned above. The cross-sectional area of the enlarged bore 1407' is determined by the desired flow rate of solution through the bore as explained above in connection with the previous embodiment.

Figure 18:
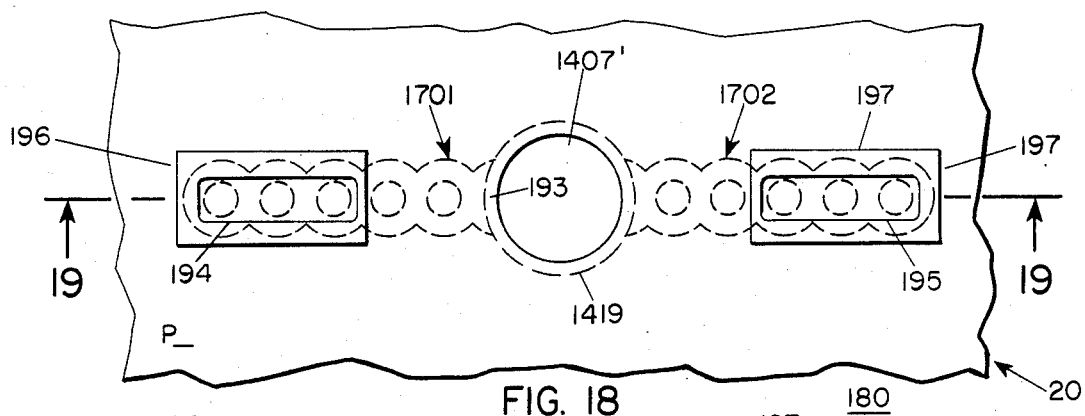
FIG. 18 is a top view of an ISFET device fabricated according to still another embodiment of the present invention.
Figure 19:
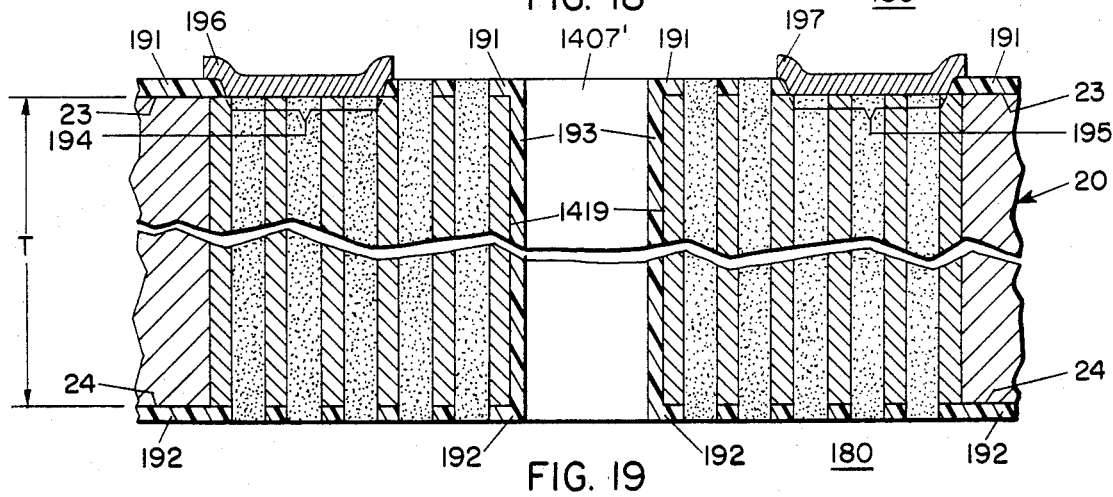
FIG. 19 is a cross-sectional view of the ISFET device of FIG. 18 taken along plane 19—19 of FIG. 18 illustrating silicon dioxide layers on the top and bottom surfaces of the device and on the inner surface of the enlarged bore, source and drain regions separated and longitudinally intersected by the enlarged bore, contact apertures for the source and drain regions in the silicon dioxide layer on the top surface, and source and drain contacts adjacent the top surface.

Turning now to FIGS. 18 and 19, having formed the enlarged bore 1407', silicon dioxide layers 191, 192 and 193 are grown on the two major surfaces 23 and 24 of the body 20 and on the inner surface 1419 of the enlarged bore 1407', respectively, using the steam oxidation technique described above. Following the oxidation step, contact apertures 194 and 195 are opened in the oxide layer 191 using conventional photolithographic and etching techniques. The contact apertures 194 and 195 expose portions of the surfaces of the $N_+$-type impurity regions 1417 and 1418, respectively, for making electrical contacts thereto. The contact apertures 194 and 195 must not overlap the P-type portions of the substrate body 20. Contacts 196 and 197 are then formed using the metallization techniques described above. Assuming that region 1701 is the source region and region 1702 is the drain region, the contacts 196 and 197 respectively serve as the connection means for the source and drain of the ISFET device 180 fabricated by the foregoing process.

The bores 1401 to 1413 are advantageously sealed using the sealing and filling technique described above in connection with the embodiment of FIGS. 2 through 7.

The silicon dioxide layer 193 on the inner surface 1419 of the enlarged bore 1407' serves as the ion-sensitive insulating layer which contacts the flowing solution being measured. As explained above in connection with the previous embodiments, the oxide layer 193 may be replaced with a layer of appropriate insulating material having ion selective membrane properties.

The contacts 135 and 136 should be spaced sufficiently far from the enlarged bore 1407' to permit effective packaging of the device 180. The nonplanar ISFET structure produced by the foregoing process permits packaging of the device for effective and reliable isolation of the contacts 196 and 197 from the solution being measured.

The channel resistance of the ISFET device 180 for a given electric field strength at the inner surface 1419 of the bore 1407' is generally proportional to the separation of the source and drain regions 1701 and 1702 and inversely proportional to the thickness T of the substrate body 20. The calculation of such channel resistance will be known in to those skilled in the art of semiconductor device design.

Referring again to FIGS. 16 and 17, the small bores 1401 to 1413 and their corresponding impurity zones 1601 to 1613 need not be disposed along a straight line as shown in FIG. 16, but may be arranged in other configurations so long as after the formation of the large bore, there are two continuous impurity regions which are separated and longitudinally intersected by the large bore. Each of the two impurity regions may comprise one or more overlapping impurity zones. In addition, it is not necessary to form the large bore by enlarging a small bore, since a large bore may be formed directly in the substrate body by the above-described laser or ultrasonic drilling techniques or other known techniques suitable for forming such a bore. Furthermore, the small bores and their corresponding impurity zones need not extend entirely through the thickness of the substrate body so long as the large bore extends all the way through the body.

The above and other modifications, alterations and substitutions may be made to the disclosed embodiments by one skilled in the art of semiconductor devices without departing from the spirit and scope of the present invention as defined by the appended claims. For example, the material of the body is not limited to single crystalline bulk silicon, as other semiconductor materials suitable for fabricating ISFET devices may be substituted. Furthermore, the semiconductor body may be initially N-type, in which case the source and drain regions are formed by the diffusion of appropriate P-type impurities.

Recent work in collaboration with NASA-Goddard has shown that the signal-to-noise ratio of x-ray imagers made by this method is an order of magnitude higher than the ratio of imagers made by previous methods.

What is claimed and sought to be protected by Letters Patent of the United States is as follows:

1. A nonplanar ISFET device comprising:
    a semiconductor body of a first conductivity type having first and second opposing major surfaces and a plurality of high-aspect-ratio, closely-spaced bores extending into the body from the first major surface thereof, including a bore with a relatively large cross-section extending between the first and second major surfaces of the body and being centrally situated among the plurality of high-aspect-ratio bores;
    first and second impurity regions of a second conductivity type in the body, each one comprising a plurality of impurity zones, each zone being substantially concentric with a respective one of the plurality of high-aspect-ratio bores and overlapping one or more neighboring zones, the first and second impurity regions being separated and longitudinally intersected by the relatively large cross-section bore;
    first and second connection means making electrical contact to the first and the second impurity regions, respectively, from the first major surface of the body, and
    an ion-sensitive insulating layer covering the inner surface of the relatively large cross-section bore.

2. The ISFET device of claim 1 wherein the first and the second connection means each comprise a metallic contact overlapping the first major surface of the body and being in contact with a respective one of the first and the second impurity regions.

3. The ISFET device of claim 1 wherein the ion-sensitive insulating layer comprises a thermally grown oxide layer covering the inner surface of the relatively large cross-section bore.

4. The ISFET device of claim 1 wherein the plurality of high-aspect-ratio bores are generally disposed along a straight line and the relatively large cross-section bore is centrally situated along the line.

5. The ISFET device of claim 1 wherein the plurality of high-aspect-ratio bores are generally disposed in an array having a plurality of regularly spaced rows and a plurality of regularly spaced columns and the relatively large cross-section bore is centrally situated in the array.

6. The ISFET device of claim 1 wherein the plurality of high-aspect-ratio bores extend completely through the thickness of the body between the first and the second major surfaces thereof, and each of the high-aspect-ratio bores are sealed with an appropriate sealing material.

7. The ISFET device of claim 1 wherein the plurality of high-aspect-ratio bores extend to within a predetermined distance of the second major surface of the body.

8. The ISFET device of claim 1 wherein the semiconductor body is monocrystalline silicon, the first conductivity type is P-type and the second conductivity type is N-type.

9. The ISFET device of claim 1 wherein the plurality of high-aspect-ratio bores are formed by laser drilling and, the relatively large cross-section bore is formed by laser drilling and selective etching.

10. The ISFET device of claim 1 wherein the plurality of high-aspect-ratio bores are formed by laser drilling and the relatively large cross-section bore is formed by laser drilling at increased laser power.

11. The ISFET device of claim 1 wherein the plurality of high-aspect-ratio bores are formed by laser drilling and the relatively large cross-section bore is formed by laser drilling of multiple overlapping bores.

12. The ISFET device of claim 2 wherein the semiconductor body is monocrystalline silicon, the first conductivity type is P-type and the second conductivity type is N-type.

13. The ISFET device of claim 2 wherein the plurality of high-aspect-ratio bores are formed by laser drilling and the relatively large cross-section bore is formed by laser drilling and selective etching.

14. The ISFET device of claim 2 wherein the plurality of high-aspect-ratio bores are formed by laser drilling and the relatively large cross-section bore is formed by laser drilling at increased laser power.

15. The ISFET device of claim 2 wherein the plurality of high-aspect-ratio bores are formed by laser drilling and the relatively large cross-section bore is formed by laser drilling of multiple overlapping bores.

* * * * *